United States Patent
Fiebel et al.

(10) Patent No.: US 11,019,988 B2
(45) Date of Patent: Jun. 1, 2021

(54) HEADLAMP

(71) Applicant: P9 VENTURES, LLC, Edgewater, NJ (US)

(72) Inventors: William Fiebel, Succasunna, NJ (US); Christopher Kanel, Hudson, NJ (US); Paul Lacotta, Tenafly, NJ (US); Steve Lucey, Greensboro, NC (US); Todd Robinson, Greensboro, NC (US)

(73) Assignee: P9 VENTURES, LLC, Edgewater, NJ (US)

( * ) Notice: Subject to any disclaimer, the term of this patent is extended or adjusted under 35 U.S.C. 154(b) by 0 days.

(21) Appl. No.: 16/448,408

(22) Filed: Jun. 21, 2019

(65) Prior Publication Data

US 2019/0313890 A1 Oct. 17, 2019

Related U.S. Application Data

(63) Continuation of application No. 13/750,270, filed on Jan. 25, 2013, now Pat. No. 10,357,146.

(60) Provisional application No. 61/590,424, filed on Jan. 25, 2012, provisional application No. 61/700,999, filed on Sep. 14, 2012.

(51) Int. Cl.
*A61B 1/06* (2006.01)
*A61B 1/00* (2006.01)
*F21V 21/096* (2006.01)
*A42B 3/04* (2006.01)
*F21V 17/10* (2006.01)
*F21V 21/084* (2006.01)

(52) U.S. Cl.
CPC .............. *A61B 1/06* (2013.01); *A61B 1/0692* (2013.01); *A42B 3/044* (2013.01); *A42B 3/0446* (2013.01); *A61B 1/00158* (2013.01); *F21V 17/105* (2013.01); *F21V 21/084* (2013.01); *F21V 21/096* (2013.01); *F21V 21/0965* (2013.01)

(58) Field of Classification Search
CPC ................................. A61B 1/06; A61B 1/0692
USPC ........... 362/581, 549, 191, 198, 249.11, 365, 362/368, 430, 103, 105, 106
See application file for complete search history.

(56) References Cited

U.S. PATENT DOCUMENTS

| | | | |
|---|---|---|---|
| 4,104,709 A | | 8/1978 | Kloots |
| 5,357,409 A | * | 10/1994 | Glatt ...................... A42B 3/044 362/105 |
| 5,973,728 A | * | 10/1999 | Levitan .................. A61B 1/267 348/376 |
| 7,008,074 B1 | * | 3/2006 | Halm ....................... A61B 1/24 362/105 |
| 7,011,439 B1 | * | 3/2006 | Kane .................... G02B 6/0008 362/269 |
| 7,314,300 B1 | | 1/2008 | Dorr et al. |
| 8,083,365 B2 | | 12/2011 | Cohen et al. |

(Continued)

FOREIGN PATENT DOCUMENTS

| WO | WO-2011137400 A1 * | 11/2011 | ............. A42B 3/044 |

OTHER PUBLICATIONS

Guideline for Disinfection and Sterilization in Healthcare Facilities, Centers for Disease Control, 2008.

*Primary Examiner* — Erin Kryukova
*Assistant Examiner* — Christopher E Dunay
(74) *Attorney, Agent, or Firm* — Cozen O'Connor

(57) ABSTRACT

A headlight device that can be mounted to a surgical face shield, helmet, or other type of headgear with dual-sided peel and stick adhesive or magnets allowing for various mounting locations.

13 Claims, 15 Drawing Sheets

(56) References Cited

U.S. PATENT DOCUMENTS

| | | | |
|---|---|---|---|
| 8,550,651 B2* | 10/2013 | Waters | A42B 1/244 |
| | | | 362/106 |
| 9,872,530 B2* | 1/2018 | Waters | F21V 33/0008 |
| 10,159,294 B2* | 12/2018 | Waters | A42B 1/244 |
| 2001/0145887 | 7/2004 | Huang | |
| 2004/0145887 A1* | 7/2004 | Huang | G02B 7/002 |
| | | | 362/105 |
| 2005/0174753 A1 | 8/2005 | Cao | |
| 2006/0133069 A1* | 6/2006 | Clupper | F21L 14/00 |
| | | | 362/106 |
| 2007/0040086 A1 | 2/2007 | Liao | |
| 2008/0310145 A1 | 12/2008 | Blake et al. | |
| 2011/0075400 A1* | 3/2011 | Lau | F21V 21/0885 |
| | | | 362/105 |
| 2011/0080725 A1* | 4/2011 | Brands | F21V 14/06 |
| | | | 362/187 |
| 2011/0157874 A1 | 6/2011 | Sant et al. | |
| 2011/0227509 A1* | 9/2011 | Saleh | A61B 1/24 |
| | | | 315/362 |
| 2012/0140459 A1 | 6/2012 | Sloan | |
| 2012/0147598 A1 | 6/2012 | Ivey | |
| 2012/0176780 A1 | 7/2012 | Gross et al. | |
| 2013/0077290 A1 | 3/2013 | HuiHui | |
| 2013/0265745 A1 | 10/2013 | Fischer | |
| 2014/0334132 A1* | 11/2014 | Ferguson | F21V 21/084 |
| | | | 362/105 |
| 2015/0003048 A1* | 1/2015 | Chang | A61B 90/35 |
| | | | 362/105 |
| 2020/0089010 A1* | 3/2020 | Koshiyama | G02B 7/12 |

* cited by examiner

Perspective View

Top View

Front View

Back View

Cross section

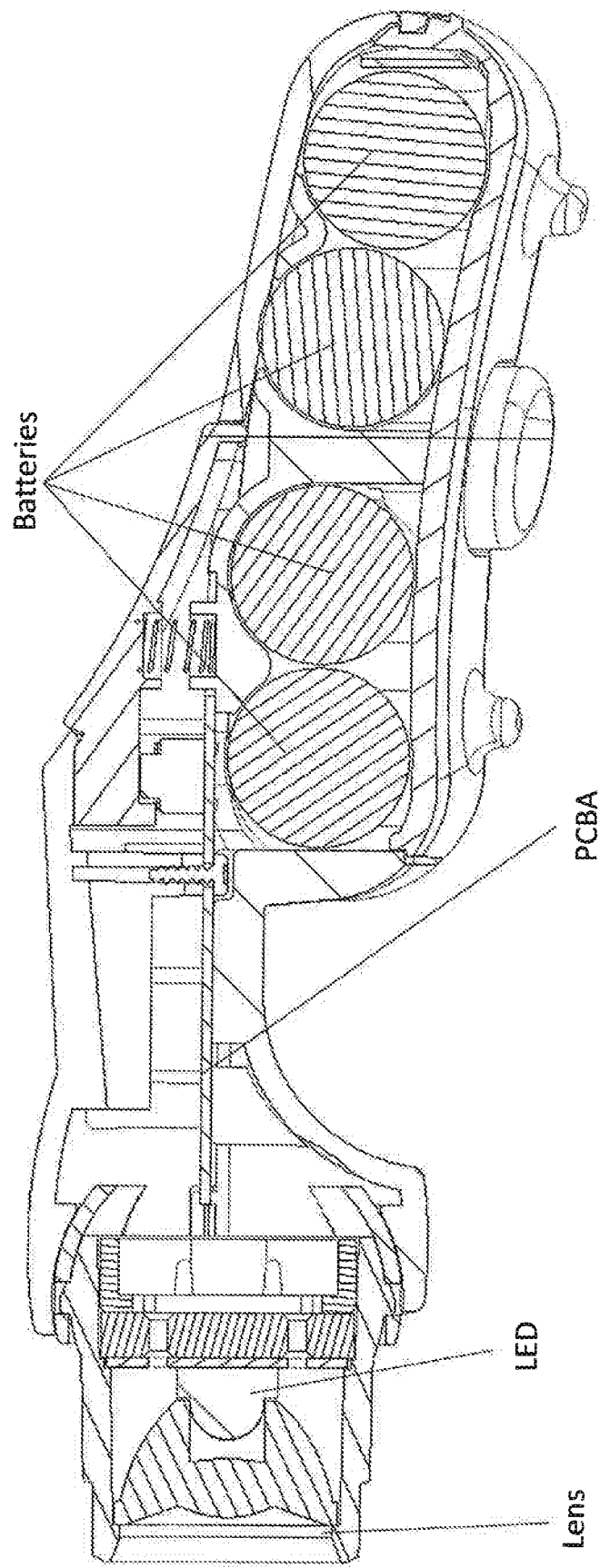

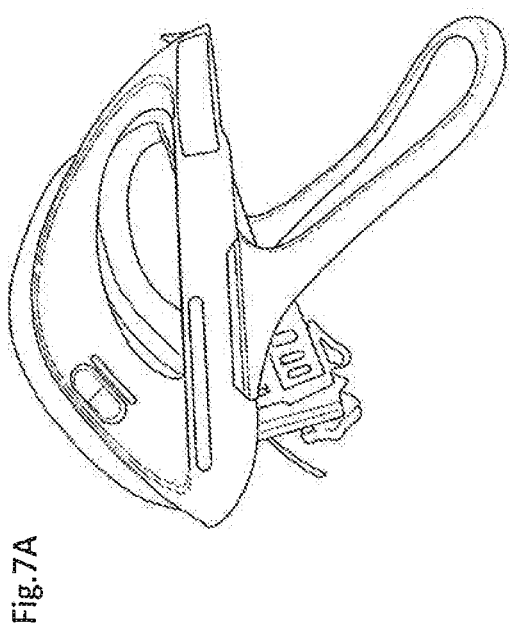

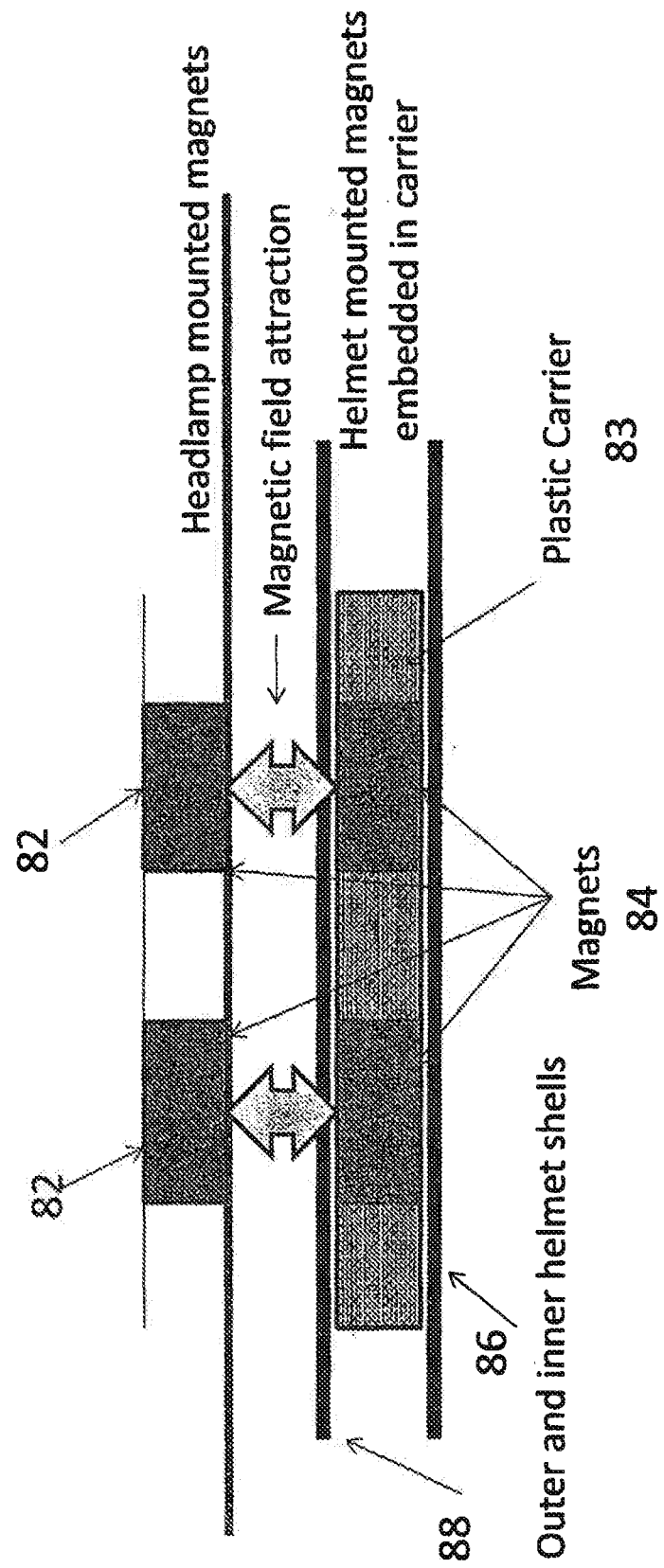
Figure 8- Schematic depiction of magnetic attachment method

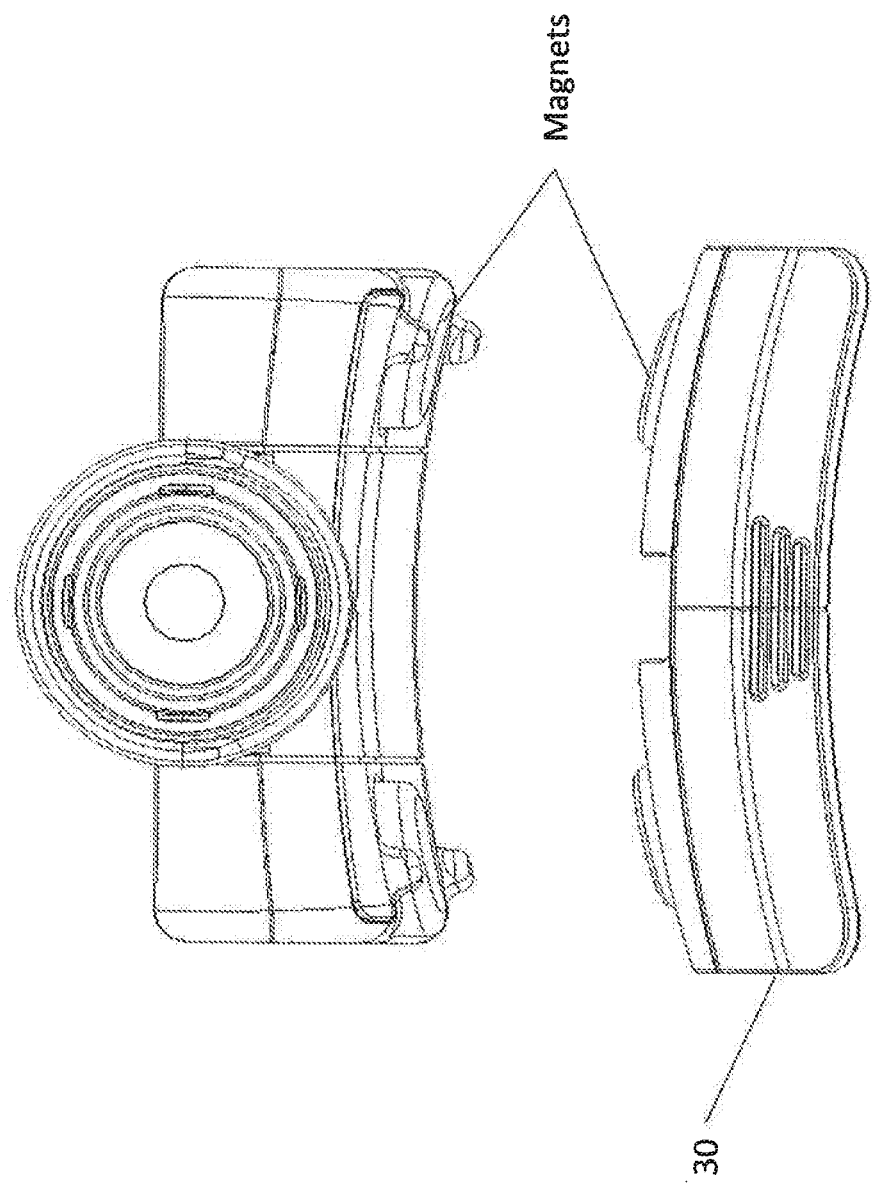

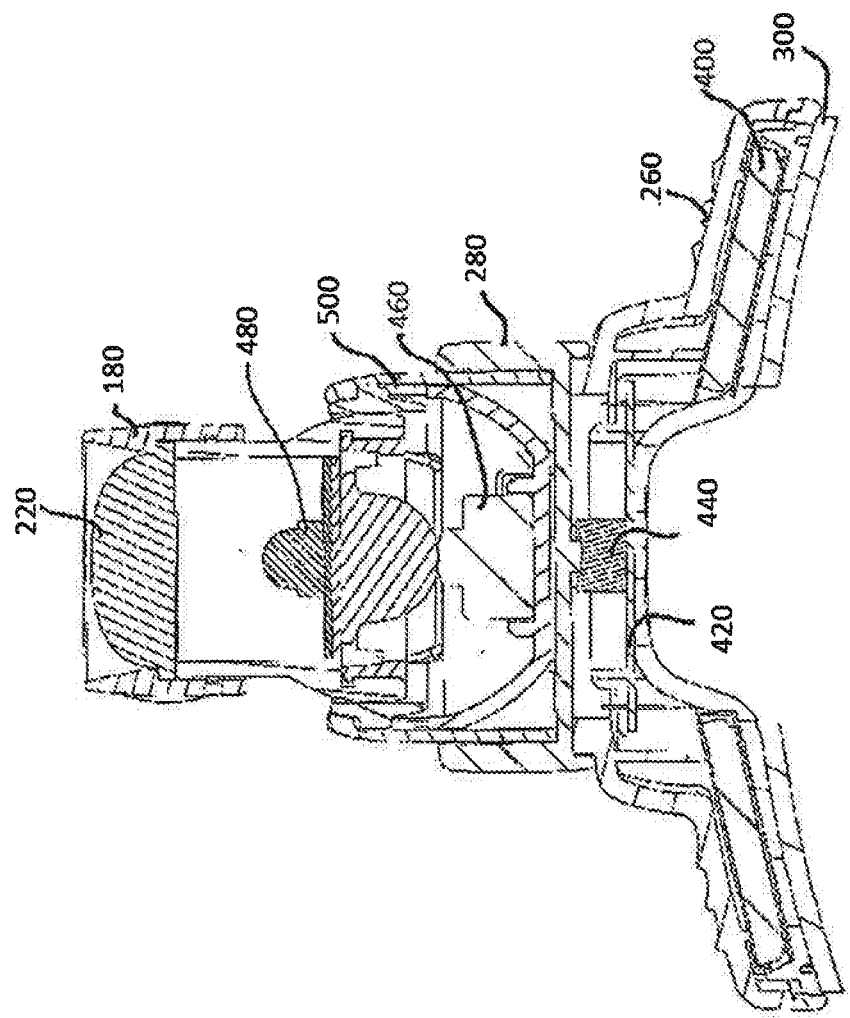

HEADLAMP

RELATED APPLICATIONS

This application is a continuation U.S. patent application Ser. No. 13/750,270 which was filed with the U.S. Patent and Trademark Office on Jan. 25, 2013. This application claims the benefit of U.S. Provisional Patent Application Ser. No. 61/590,424 which was filed on Jan. 25, 2012 and U.S. Provisional Patent Application Ser. No. 61/700,999 which was filed on Sep. 14, 2012, their subject matter incorporated herein by reference.

BACKGROUND OF THE INVENTION

1. Field of the Invention

The present invention is directed to a headlight and more particularly to a removeable headlamp.

2. Description of the Related Art

Surgical headlamps or headlights are known that are mounted to a headband. These headlamps typically have a remote light source that is connected to the headlamp via a fiber optic cable. These headlamps are usually adjustable when worn on a user's head so that the headlamp is positioned at a desired location on the user's head.

Battery powered, headlamps utilizing an incandescent lamp as a light source have also been used. Typically, the high power consumption, relatively low light output, high weight, and short battery life of such devices have made their use unsatisfactory.

In modern operating rooms and dental offices, doctors, surgeons, nurses, anesthesiologists, technicians, and the like, wear face shields. These face shields, interfere with prior art headlamps.

The user is unable to wear both the banded headlamp and the banded face shield. Further, if the headlamp is configured to attach to a pair of eye glasses or is integrally formed in an eye glass frame, glare from the headlamp on the inside of the face shield can interfere with the wearer's field of view. Additionally, if the headlamp does not have an extremely low profile, the face shield will not sit properly over a user's face and provide the intended protection to the user.

SUMMARY OF THE INVENTION

In accordance with one embodiment of the present invention, a surgical headlight is provided that overcomes the problems of headlamps of the prior art.

At least one lamp housing is provided. The lamp housing has four mounting points and two magnet attach points on the underside arranged to conform to the contour of the helmet. This or similar such arrangements help maintain uniform contact across the helmet surface.

In embodiment, the spot size adjuster and the brightness control are coaxially arranged on the lamp housing and are accessible from all sides.

In one embodiment, the disclosed headlamp is sterile, disposable, and delivered to a user in a sterile package.

The surgical headlamp can also be mounted to a surgical face shield, helmet, or other type of headgear with dual-sided peel and stick adhesive that allow for various mounting locations.

In one embodiment, coaxially located adjustment features allow for a variety of mounting configurations while maintaining symmetry of access to controls of the surgical headlamp with either the left or right hand. A light aiming mechanism comprises of a ball pivot with an integral lens. Spot size adjustment is controlled by varying the distance between a single lens and the LED. A coaxially mounted brightness control is provided.

The surgical headlamp is energy efficient using pulse width modulation technique for brightness control. Batteries preferably provide power.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

FIGS. 6A and 6B is a cross section of the headlamp;
FIGS. 7A-7C depict a helmet;
FIG. 8 is a schematic depiction of a magnetic mount;
FIG. 11 is a headlamp with a combined adhesive and magnetic mount;
FIG. 13 is a cross section of the headlamp of FIG. 12.

DETAILED DESCRIPTION OF THE PRESENTLY PREFERRED EMBODIMENTS

The disclosed surgical headlamp is preferably a self-contained, disposable, LED light, which is battery powered. The headlamp provides on the spot supplemental lighting for surgery. While the surgical headlamp can be reused, it is intended to be a single use disposable device. Preferably, due to plastic material choice, the headlamp is lightweight.

The surgical headlamp features a ball pivot to adjust the focus point or aimpoint of the illuminated field. The surgical headlamp is also lightweight due to its construction. An on/off switch allows the user to turn the surgical headlamp off when it is not needed. A variable brightness control allows the user to adjust the brightness as required, which could be a separate control. A discrete brightness control may also be integrated with the on/off switch, which provides successive brightness settings with each push of the button. For example, the first push turns the lamp on and sets brightness at 25%, the next push sets it to 50%, the next to 75%, the next to 100%, the next cycles back to off. More or less brightness setting selections may also be provided for.

Given the variety of face shields, the surgical headlamp may provide a peel and stick adhesive for mounting. Finally, the surgical headlamp is sterile and ready to use out of the box.

Figure 1:
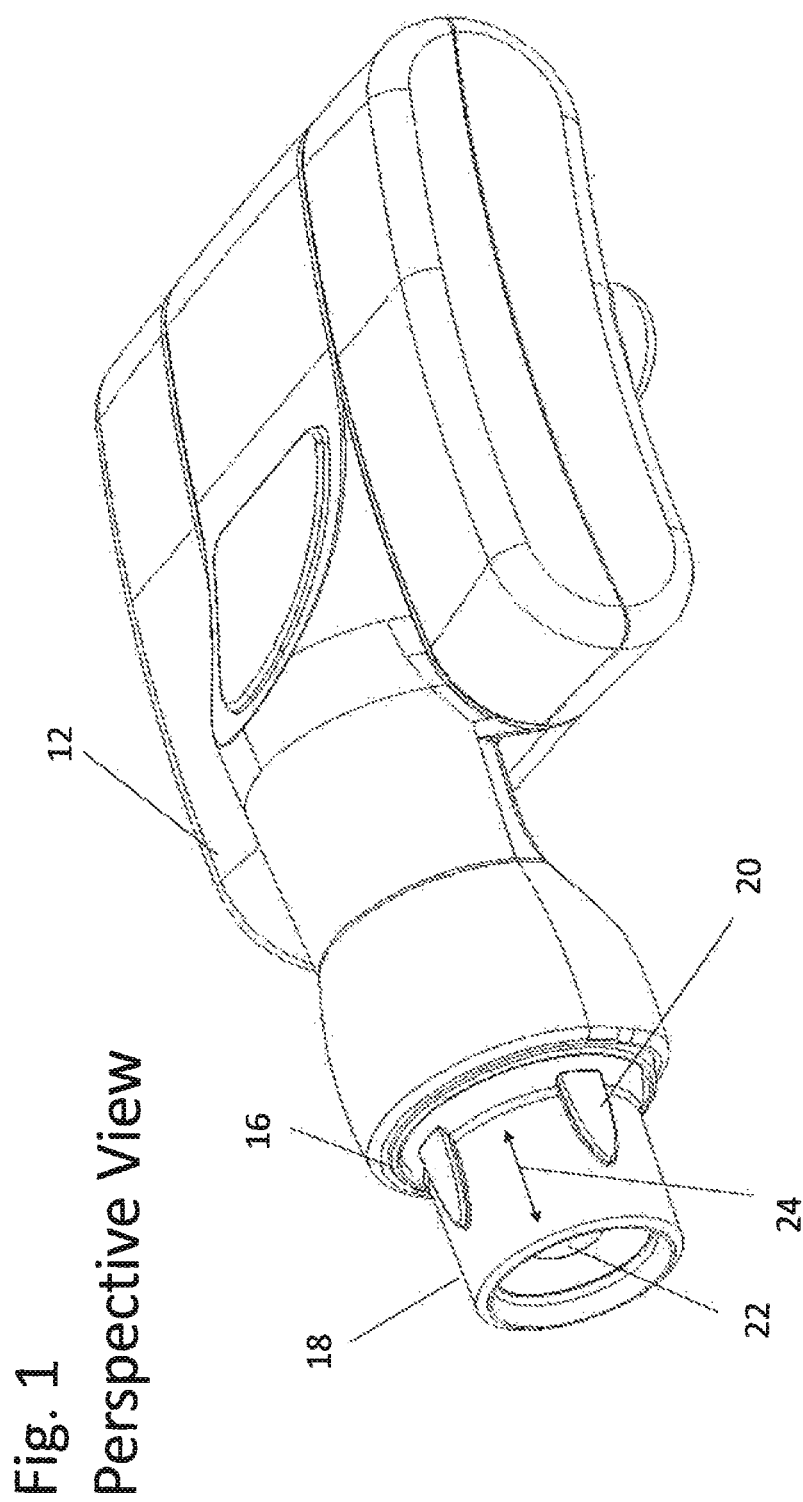
FIG. 1 is a perspective view of the headlamp.

FIG. 1 is a first embodiment of the inventive surgical headlamp 10. As shown, a single lamp housing 12 is provided. The lamp housing 12 has a directional aiming portion 14, preferably provided by a ball pivot 16. The aiming portion 14 may include a spot size adjuster 18. Preferably, the spot size adjuster is rotated using integral grips 20. Rotation of the spot size adjuster moves lens 22 in an axial direction shown by double arrow 24. In one embodiment, the spot size adjustment moves about 4-8 mm, which varies the spot size from about 5 inches to about 8 inches in diameter at two feet distance from the lamp. In one embodiment, the spot size adjustment 18 incorporates a push switch to turn the headlamp 10 on and off. In another embodiment, as the spot size adjustment 18 is rotated the headlamp 10 first turns on, then the spot size is adjusted from either its maximum or minimum to its other size extreme.

It should be noted that lens 22 is a polycarbonate or PMMA plastic lens. An achromatic glass lens is preferably used to limit chromatic and spherical aberration. In one embodiment, an achromatic doublet is used as lens 22.

Lamp housing 12 further comprises a variable brightness control. Like the spot size adjuster 18, the variable brightness control 28 includes grips 20. In one embodiment, the variable brightness control is coupled to a variable resistor. The variable resistor is part of a pulse width modulated (PWM) drive for a light emitting diode (LED) arranged in lamp housing 12. The variable resistor varies the duty cycle of the drive signal thereby varying the brightness. Alternatively, the variable brightness control can control an iris, which varies the opening size.

To mount the lamp housing 12 to a surgical faceplate, the lamp housing 12 may be provided with wings, which can pivot to accommodate surgical faceplates having varying arcs. The lamp housing 12 can be affixed using peel and stick tape 30. In one embodiment, the tape 30 is thick enough to accommodate varying faceplate arcs.

Figure 2:
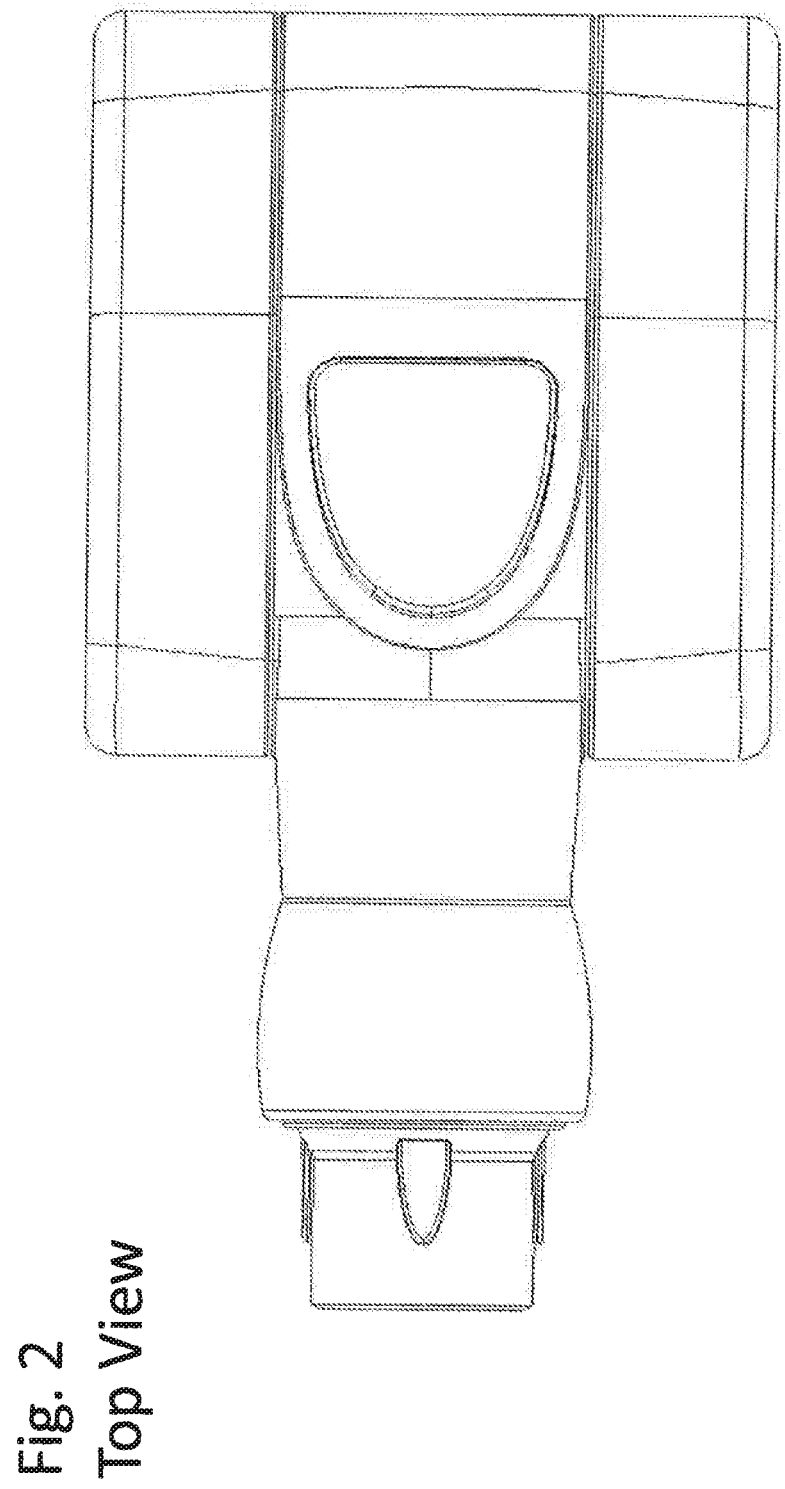
FIG. 2 is a top view of the headlamp.

A top view of the surgical headlamp 10 is shown in FIG. 2. As shown, the ball pivot 16 is configured to have a greater range in a vertical direction than a horizontal direction. It should be noted that the lamp housing 12 can be shaped to provide specific travel tracks for the ball pivot 16 or equal movement in all directions.

Figure 3:
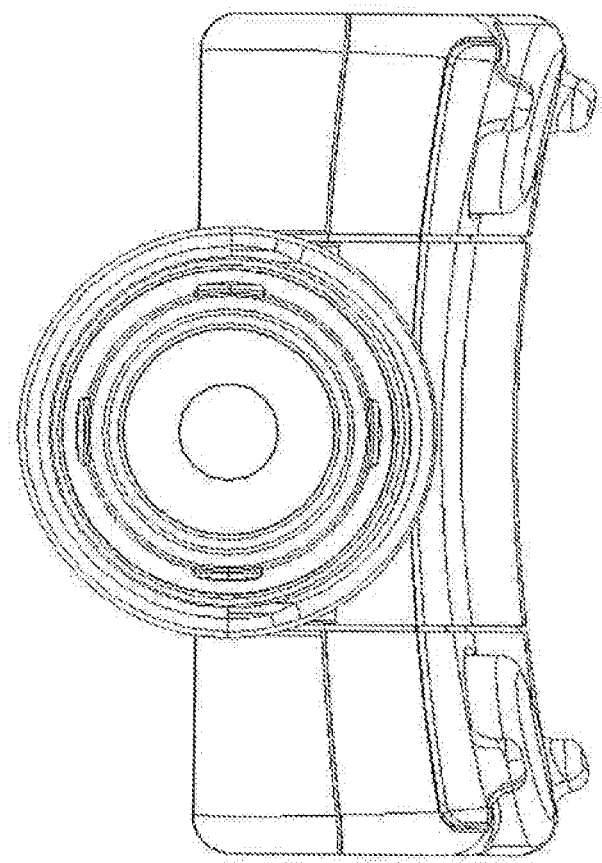
FIG. 3 is a front view of the headlamp.
Figure 4:
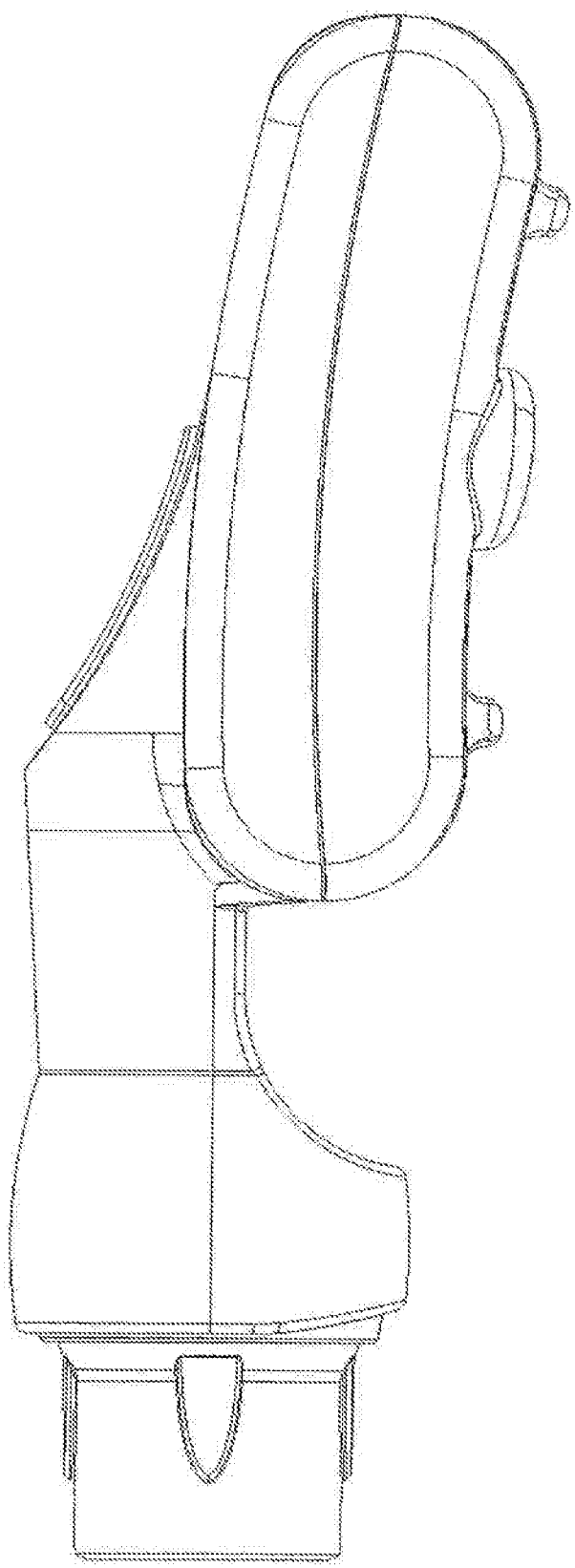
FIG. 4 is a side view of the headlamp.
Figure 5:
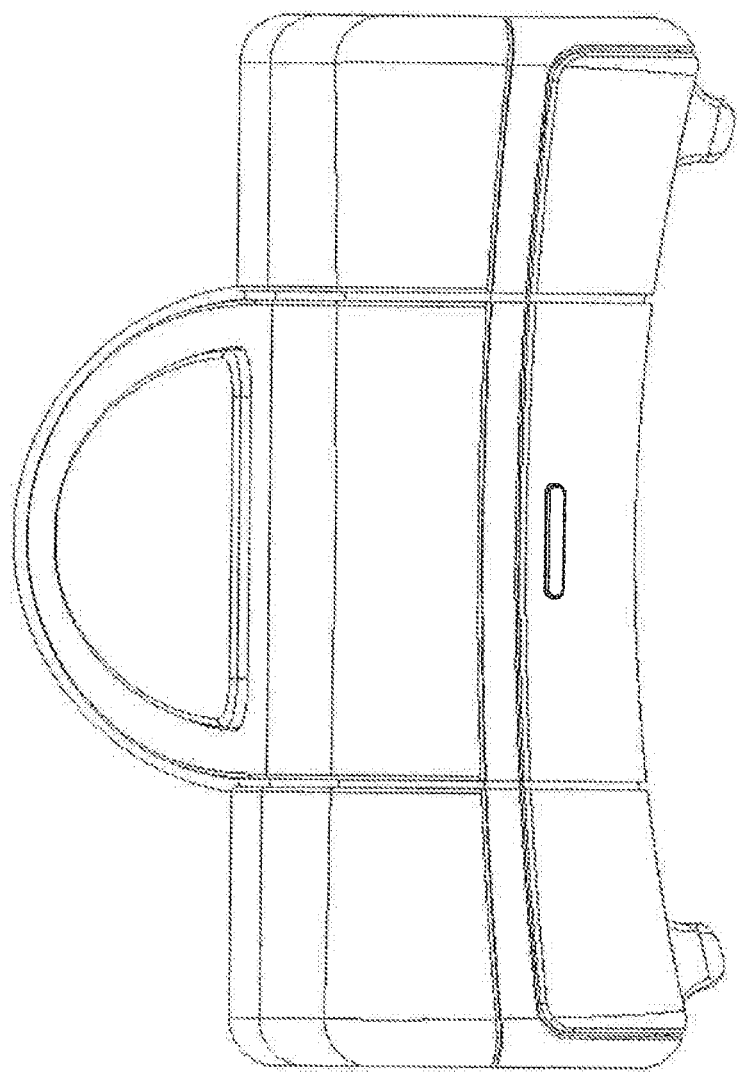
FIG. 5 is a back view of the headlamp.
Figure 6A:
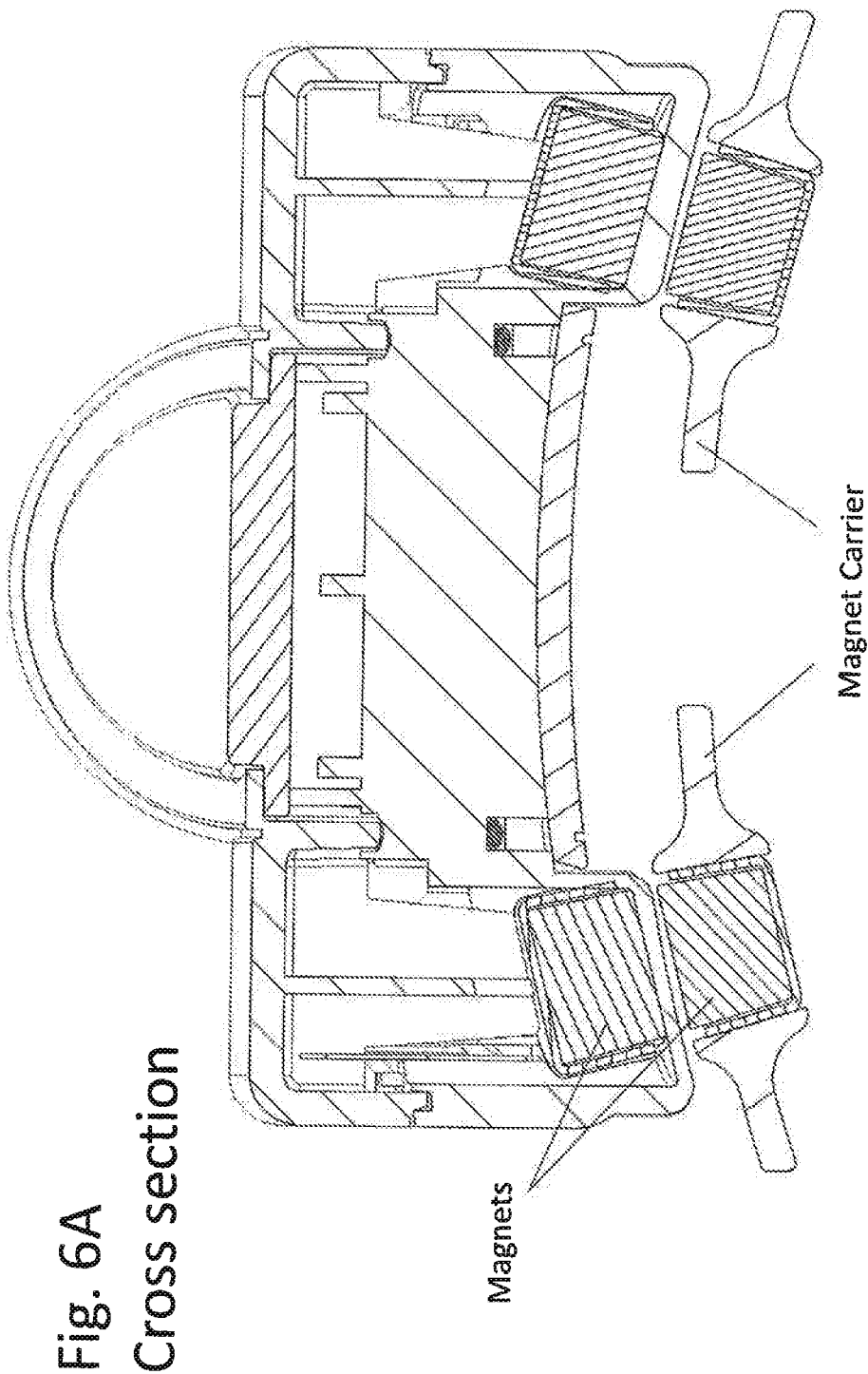

As is evident from FIG. 3, the components are arranged coaxially or on a centerline as described from the front to the rear of the headlamp. In this manner, all of the adjustments can be accessed by either hand and from any direction.

In alternative embodiments, the surgical headlamp 10 is mounted using clips. In one embodiment, the wings 26 are hinged or flexible to move about 10°.

In use, a sealed package containing the headlamp 10 is opened. The package is pre-sealed and the headlamp 10 is a sterile device. In a preferred embodiment, the headlamp 10 is manufactured from components that can be sterilized using gamma radiation. In one embodiment, the headlamp 10 is removed from its sterile package, coverings from adhesive pads 30 located on the mounting wings are removed. The headlamp 10 is positioned on a face shield and installed. The user then pushes the lens assembly to turn on the headlamp 10 and pushes the lens assembly again to turn off headlamp 10.

The lens housing, which is the spot size adjuster 18, serves as a beam director and on/off switch. By avoiding a separate switch, this headlamp 10 can be activated by a finger or by pressing, for example, with the back of a hand or wrist. Once on, the headlamp 10 can be pointed to a desired position. The spot size control 18 can be rotated to the desired size and the brightness control 28 can be rotated to achieve the desired brightness. After use, headlamp 10 can be disposed of.

In non-sterile environments, and for non-sterile requirements, the headlamp 10 can be reused. In one embodiment, the headlamp 10 is returned for reconditioning including replacing used batteries and undergoing gamma radiation and sterile packaging. While disclosed as a sterile surgical headlamp. The present headlamp can be used in any application when a head-mounted light is required.

In one embodiment, multiple LEDs are provided in a single lamp housing 12. In one embodiment, stereo illumination is provided.

In one embodiment, a magnetic attachment method replaces the peel and stick mounting method. The magnetic mounting method is preferred for mounting the headlamp device to a surgical helmet covered with a cloth material.

As shown schematically in FIG. 8, one or more magnets 82 are located internally to the headlamp, and one or more magnets 84, which are located inside a helmet, attract each other allowing for secure attachment of the headlamp to the helmet. It should be noted that the helmet can be a strap, hood, or the like.

The helmet, to which the headlamp is mounted, has an inner shell 86 and outer shell 88. The gap between the shells allows for insertion of a second set of magnets in between them by a plastic magnet carrier 83. Once inserted in the gap between the inner shell 86 and the outer shell 88, the magnets 84 are not visible to the user.

The location of the magnets 84 in the magnet carrier 83 that is inserted into the helmet and the magnets 82 internal to the headlamp are designed to be coaxially aligned so as to position each respective magnet set over the other set to maximize the alignment of magnetic fields for maximum attraction. Once the headlamp is positioned over the magnets internal to the helmet, the magnetic fields naturally align and attract, attaching the headlamp securely to the helmet. In one embodiment, a steel shield is used to help focus the magnetic fields of the respective helmet and headlamp magnets in such as manner to maximize magnetic coupling.

In one embodiment, the headlamp has magnets arranged on an underside of the headlamp assembly. A magnet bracket adapted to fit in a helmet is shown. In one embodiment, ridges are provided to hold the magnet bracket between an inner and outer shell of the helmet. In one embodiment, the magnet bracket has aligning elements for aligning the headlamp and bracket.

As shown, magnets are under the plastic housing of the headlamp. In one embodiment, the housing is injection molded with the magnets. In another embodiment, the magnets are arranged inside the housing.

In one embodiment, the magnets are affixed to an outside surface of the housing using an adhesive. In this embodiment, a user can choose between an adhesive mount and/or a magnetic mount.

Figure 9:
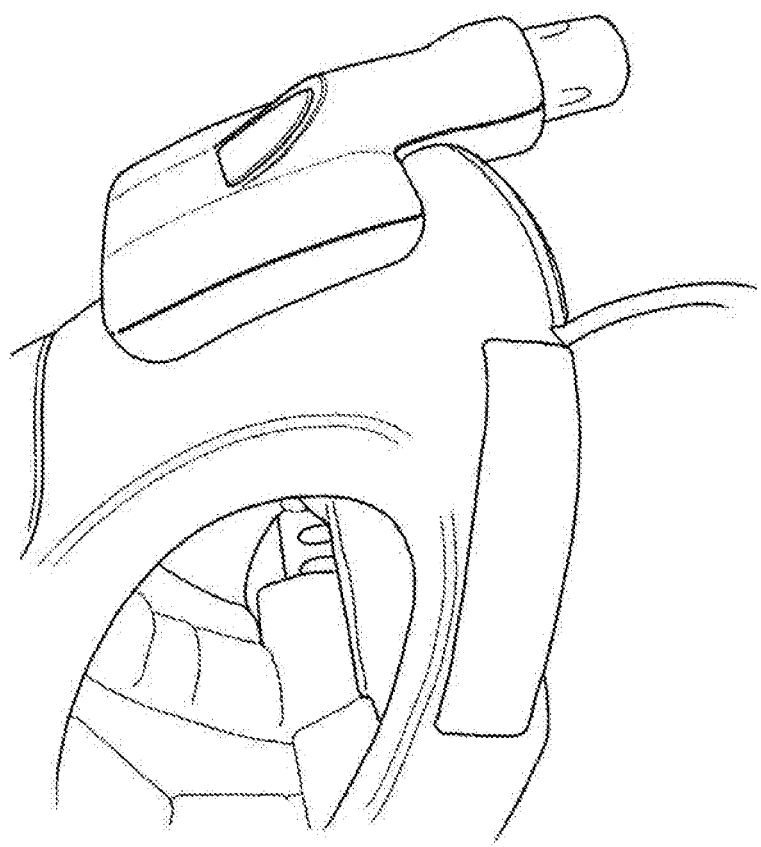
FIG. 9 is the headlamp with the lamp mounted.
Figure 10A:
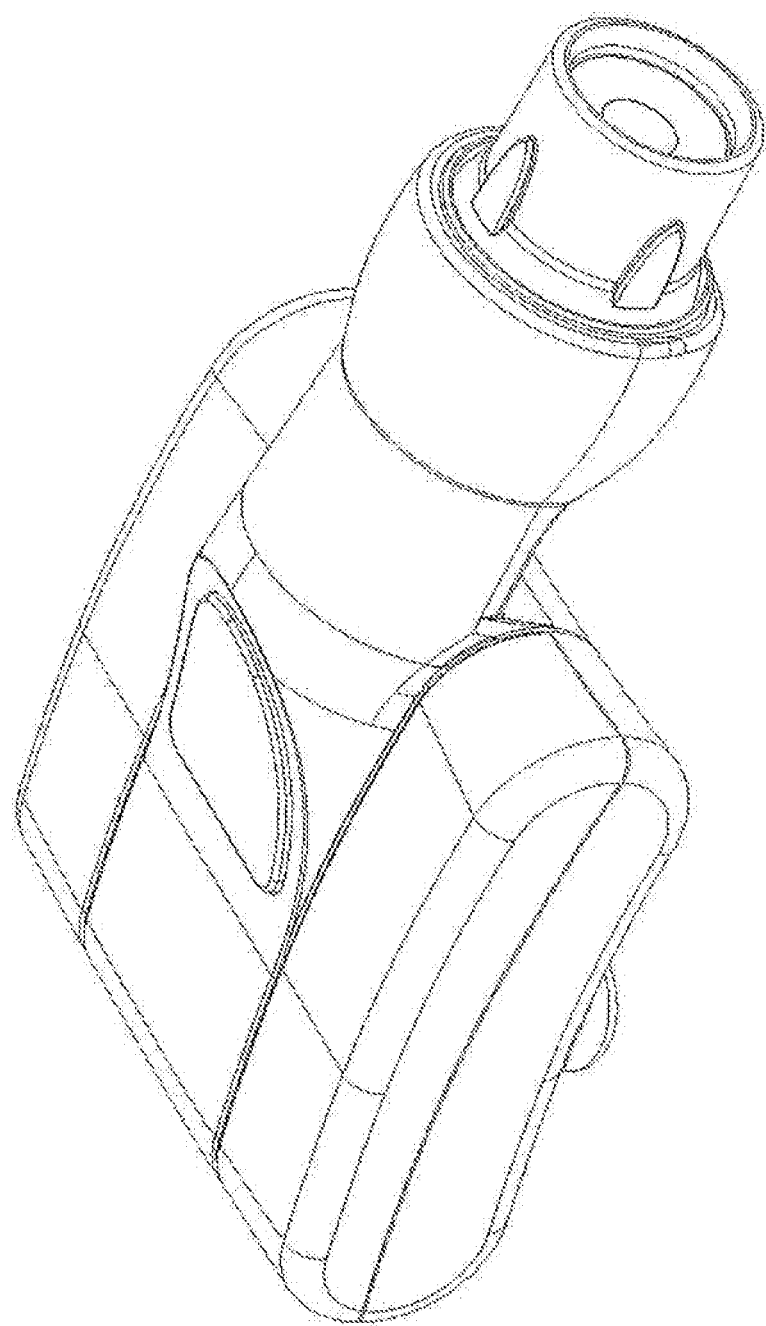
FIGS. 10A and 10B are another view of the headlamp of FIG. 9.
Figure 10B:
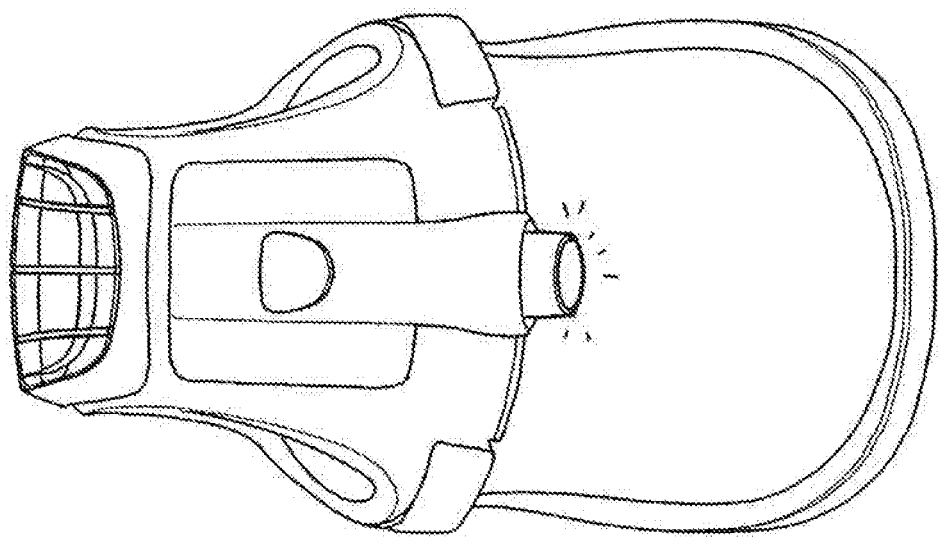

FIG. 9 is a helmet with the lamp mounted thereon. FIG. 10 is another view of the headlamp mounted to a helmet.

FIG. 11 is another embodiment of the headlamp. An adhesive mount is provided so that the headlamp can be mounted to virtually any surface. The adhesive mount is contoured to mate with the headlamp. Due to the contouring, the headlamp is limited in its lateral movement. The headlamp and the adhesive mount preferably have matching magnetic mounting elements.

Figure 12:
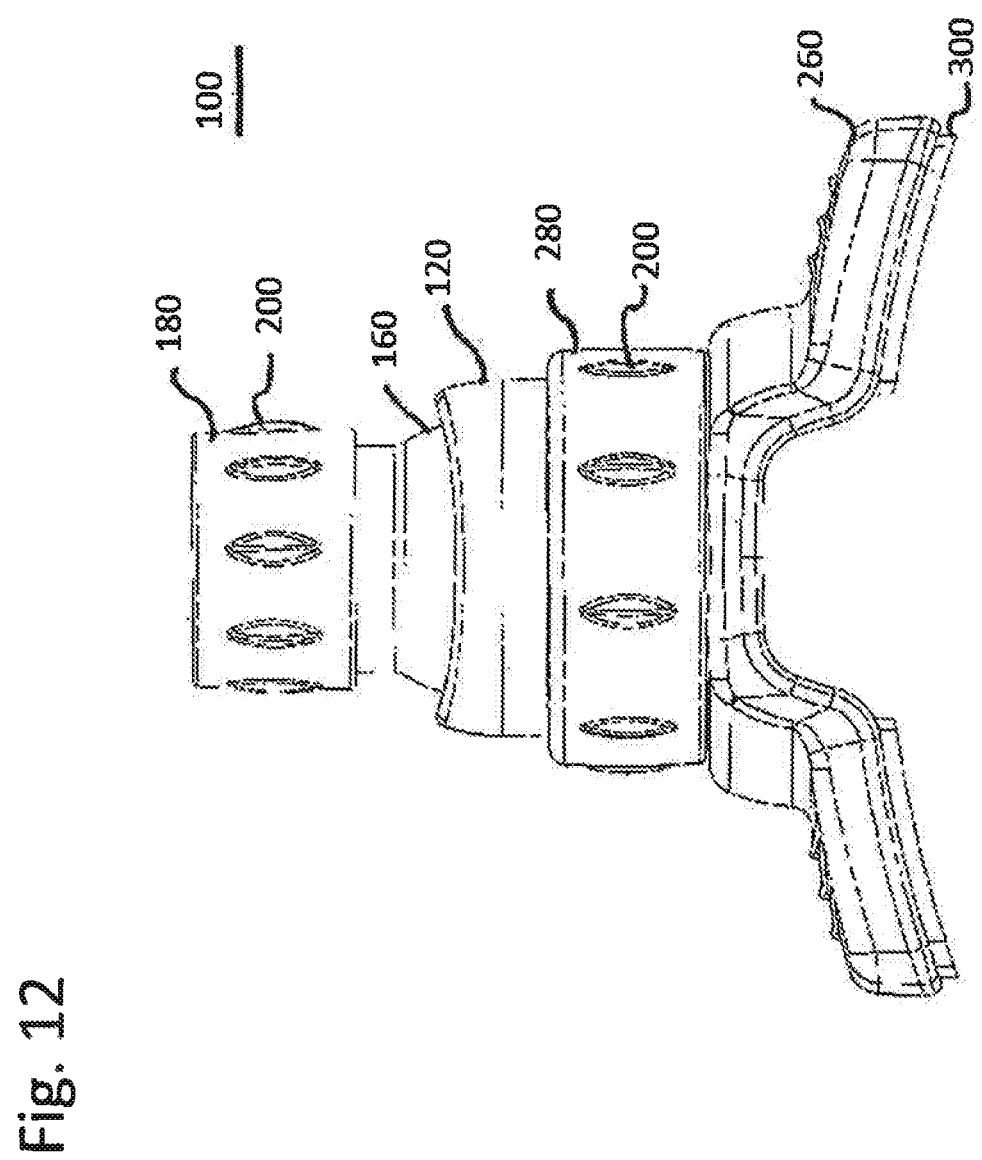
FIG. 12 is a top view of a headlamp.

FIG. 12 is another embodiment of surgical headlamp 100. As shown a single lamp housing 120 is provided. The lamp housing 120 has a directional aiming portion preferably provided by a ball pivot 160. The aiming portion includes a spot size adjuster 180. Preferably, the spot size adjuster is rotated using grips 200. Rotation of the spot size adjuster moves lens 220 in an axial direction. In a preferred embodiment, the spot sized moves about 4-8 mm, which varies the spot size from about 5 inches to about 8 inches at two feet. In one embodiment, the spot size adjustment 180 is a push switch to turn the headlamp 100 on and off. In another embodiment, as the spot size adjustment 180 is rotated the headlamp 100 first turns on, then the spot size is adjusted from either its maximum or minimum to its other size extreme.

It should be noted that lens 220 is preferably a polycarbonate lens. An achromatic lens is preferably used to limit chromatic and spherical aberration. In one embodiment, an achromatic doublet is used as lens 220.

Lamp housing 120 further comprises a variable brightness control 280. Like the spot size adjuster 180, the variable brightness control 280 includes grips 200. In a preferred embodiment, the variable brightness control is coupled to a variable resistor. The variable resistor is part of a pulse width modulated (PWM) drive for a light emitting diode (LED) arranged in lamp housing 120. The variable resistor varies the duty cycle of the drive signal thereby varying the brightness. Alternatively, the variable brightness control 280 can control an iris.

To mount the lamp housing 120 to a surgical face plate, the lamp housing 120 is provided with wings 260. In a preferred embodiment, the wings 260 can pivot to accommodate surgical face plates having varying arcs. The lamp housing 120 is affixed using peel and stick tape 300. In one embodiment, the tape 300 is thick enough to accommodate varying face plate arcs. Preferably, the components are arranged coaxially. In this manner, all of the adjustments can be accessed by either hand and from any direction.

FIG. 13 is a cross section of the surgical headlamp 100. As shown, coin batteries 400 are preferably arranged in the mounting wings 260. The coin batteries 400 are coupled to PC board 420 which includes the potentiometer 440 for the PWM circuit discussed above. As shown, when a force is applied to the spot size adjuster 180, the entire assembly is able to move towards the mounting wings 260 guided in area 500. This movement depresses a switch 460 to turn LED 48 on and off.

In alternative embodiments, the surgical headlamp 10, 100 is mounted using clips. In one embodiment, the wings are hinged or flexible to move about 10°.

In one embodiment, the housing containing the magnets is affixed to the outside of the surgical helmet with an adhesive mount. The geometry of the mount and of the matching underside of the headlamp is such that in order to remove the headlamp, the user must pull the headlamp away from the mount along the axis of magnetic attraction thus preventing inadvertent removal by sliding the headlamp sideways.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A sterilizable lighting device, comprising:
a headgear device having an outer shell and a plurality of magnetic mounting elements disposed below the outer shell and spaced apart from one another in a plurality of locations;
a headlight device comprising:
a housing,
a magnetic mounting portion coupled to the housing comprising a magnet,
a lens assembly coupled to the housing, wherein the lens assembly comprises at least one lens and a ball pivot aiming mechanism, the ball pivot aiming mechanism comprising a ball pivot,
a light source at least partially coaxially aligned with the at least one lens inside the ball pivot, wherein the light source comprises at least one LED arranged directly adjacent to the at least one lens and configured to project light through the at least one lens, and
a switch for the light source;
wherein the magnetic mounting portion is configured to magnetically couple to the plurality of magnetic mounting elements, the headlight device is mountable in each of the plurality of locations, and the plurality of magnetic mounting elements are arranged in the headgear device such that the headlight device is arrangeable to be mounted in a plurality of locations.

2. The sterilizable lighting device of claim 1, wherein the magnets are at least one of embedded in the housing or attached to the housing.

3. The sterilizable lighting device of claim 2, further comprising an external mount configured to magnetically retain the housing, wherein the housing is configured to be separated from the external mount by pulling the headlamp away along an axis of magnetic attraction.

4. The sterilizable lighting device of claim 1, wherein the lighting device is sterile.

5. The sterilizable lighting device of claim 1, wherein the at least one LED is driven by a pulse width modulated driver circuit.

6. The sterilizable lighting device of claim 1, wherein the light aiming mechanism further comprises an integral on/off switch.

7. The sterilizable lighting device of claim 6, wherein the on/off switch is a push switch.

8. The sterilizable lighting device of claim 1, wherein the ball pivot has integral coaxial beam spot size adjustment, wherein spot size adjustment is controlled by varying a distance between the lens assembly and the light source.

9. The sterilizable lighting device of claim 8, further comprising a coaxially mounted brightness control mounted to the lens assembly.

10. The sterilizable lighting device of claim 1, wherein the lens assembly comprises one or more of a polycarbonate lens, a PMNA plastic lens, an achromatic glass lens, and an achromatic doublet.

11. A sterilizable lighting device, comprising:
a headgear device having an outer shell and a plurality of magnetic mounting elements disposed below the outer shell and spaced apart from one another in a plurality of locations;
a headlight device comprising:
   a housing,
   a magnetic mounting portion coupled to the housing comprising a magnet,
   a lens assembly coupled to the housing, wherein the lens assembly comprises a ball pivot aiming mechanism, the ball pivot aiming mechanism comprising a ball pivot,
   a light source at least partially coaxially aligned with the at least one lens inside the ball pivot, wherein the light source comprises at least one LED arranged adjacent to a lens of the lens assembly and configured to project light through the lens assembly and the ball pivot that illuminates a field, and
   a switch for the light source;
wherein the magnetic mounting portion is configured to magnetically couple to the plurality of magnetic mounting elements, the headlight device is mountable in each of the plurality of locations, and the plurality of magnetic mounting elements arranged in the headgear device provide a plurality of mounting locations for mounting the headlight device.

12. The sterilizable lighting device of claim 11, wherein the light source is arranged at least partially inside lens assembly.

13. A sterilizable lighting assembly, comprising:
a sterile headgear comprising an outer shell and a plurality of magnetic mounting elements disposed below the outer shell;
a face shield affixed to the sterile headgear; and
a headlight device configured to be mounted to the headgear comprising:
   a housing comprising a sterilizeable plastic having a magnetic mounting portion containing a magnet,
   a lens assembly coupled to the housing, wherein the lens assembly comprises at least one lens and a ball pivot aiming mechanism, the ball pivot aiming mechanism comprising a ball pivot,
   a light source at least partially coaxially aligned with the at least one lens inside the ball pivot and arranged directly adjacent to the at least one lens and configured to project light through the at least one lens, and
   a switch for the light source;
wherein the magnetic mounting portion of the headlight is configured to magnetically couple to the plurality of magnetic mounting elements of the headgear device with a barrier of the face shield disposed therebetween, the headlight device is mountable in each of the plurality of locations, and the plurality of magnetic mounting elements provide a plurality of mounting locations such that the headlight device is configured to mount to the headgear device at a plurality of locations.

* * * * *